(12) United States Patent
Blase

(10) Patent No.: US 9,770,161 B2
(45) Date of Patent: Sep. 26, 2017

(54) JOINTED PORTION OF A SHAFT FOR AN ENDOSCOPIC INSTRUMENT

(75) Inventor: Bastian Blase, Berlin (DE)

(73) Assignee: Karl Storz GmbH & Co. KG (DE)

( * ) Notice: Subject to any disclaimer, the term of this patent is extended or adjusted under 35 U.S.C. 154(b) by 641 days.

(21) Appl. No.: 13/208,968

(22) Filed: Aug. 12, 2011

(65) Prior Publication Data

US 2012/0041264 A1 Feb. 16, 2012

(30) Foreign Application Priority Data

Aug. 13, 2010 (DE) ........................ 10 2010 034 380

(51) Int. Cl.

| | |
|---|---|
| *A61B 1/00* | (2006.01) |
| *A61B 1/008* | (2006.01) |
| *A61B 1/12* | (2006.01) |
| *A61B 5/06* | (2006.01) |
| *A61B 1/06* | (2006.01) |
| *A61B 1/005* | (2006.01) |
| *A61B 1/055* | (2006.01) |

(52) U.S. Cl.
CPC ............ *A61B 1/008* (2013.01); *A61B 1/0057* (2013.01); *A61B 1/00078* (2013.01); *A61B 1/06* (2013.01); *A61B 1/126* (2013.01); *A61B 1/127* (2013.01); *A61B 1/128* (2013.01); *A61B 5/065* (2013.01); *A61B 1/055* (2013.01)

(58) Field of Classification Search
CPC ... A61B 1/0055; A61B 1/008; A61B 1/00071; A61B 1/0051; A61B 1/0052; A61B 1/05; A61B 1/31

USPC ............... 600/111, 121, 205, 137, 141–142; 606/142, 205, 209
See application file for complete search history.

(56) References Cited

U.S. PATENT DOCUMENTS

| | | | |
|---|---|---|---|
| 5,885,207 A | 3/1999 | Iwasaka | |
| 6,036,636 A * | 3/2000 | Motoki et al. | ............... 600/146 |
| 6,270,453 B1 | 8/2001 | Sakai | |
| 6,270,508 B1 * | 8/2001 | Klieman | .............. A61B 17/062 |
| | | | 606/147 |
| 6,454,703 B1 * | 9/2002 | Ide | ............................... 600/142 |
| 6,482,149 B1 | 11/2002 | Torii | |
| 6,503,193 B1 | 1/2003 | Iwasaki et al. | |

(Continued)

FOREIGN PATENT DOCUMENTS

| | | |
|---|---|---|
| DE | 10143966 B4 | 1/2007 |
| EP | 0017016 A1 | 10/1980 |

(Continued)

OTHER PUBLICATIONS

European Search Report; Application No. EP 11 17 7168; Issued: May 15, 2012; Mailing Date: May 24, 2012; 6 pages.

(Continued)

*Primary Examiner* — John P Leubecker
*Assistant Examiner* — Rajaa El Alami
(74) *Attorney, Agent, or Firm* — Whitmyer IP Group LLC

(57) ABSTRACT

An endoscopic instrument, in particular an endoscope, with a jointed portion of a shaft for connecting a distal part of the shaft with a proximal part of the shaft in a way to be angulated. For this purpose, the distal shaft part is connected with the proximal shaft part by two rigid jointed bars of different lengths, wherein each of the rigid jointed bars attaches with a joint on the distal shaft part and a joint on the proximal shaft part.

17 Claims, 8 Drawing Sheets

(56) References Cited

U.S. PATENT DOCUMENTS

| | | |
|---|---|---|
| 6,749,560 B1 | 6/2004 | Konstorum et al. |
| 6,860,849 B2 | 3/2005 | Matsushita et al. |
| 8,377,059 B2* | 2/2013 | Deville et al. .................. 606/45 |
| 2003/0065358 A1 | 4/2003 | Frecker et al. |
| 2007/0055103 A1 | 3/2007 | Hoefig et al. |
| 2008/0027279 A1 | 1/2008 | Abou El Kheir |
| 2011/0087269 A1* | 4/2011 | Stokes ................... A61B 17/29 |
| | | 606/206 |

FOREIGN PATENT DOCUMENTS

| | | |
|---|---|---|
| EP | 1849400 A1 | 10/2007 |
| EP | 1927312 A1 | 6/2008 |
| WO | 2007102152 A2 | 9/2007 |
| WO | 2008060075 A1 | 5/2008 |

OTHER PUBLICATIONS

German Search Report; Application No. DE 10 2010 034 380.3; Issued: Nov. 5, 2010; 3 pages.

* cited by examiner

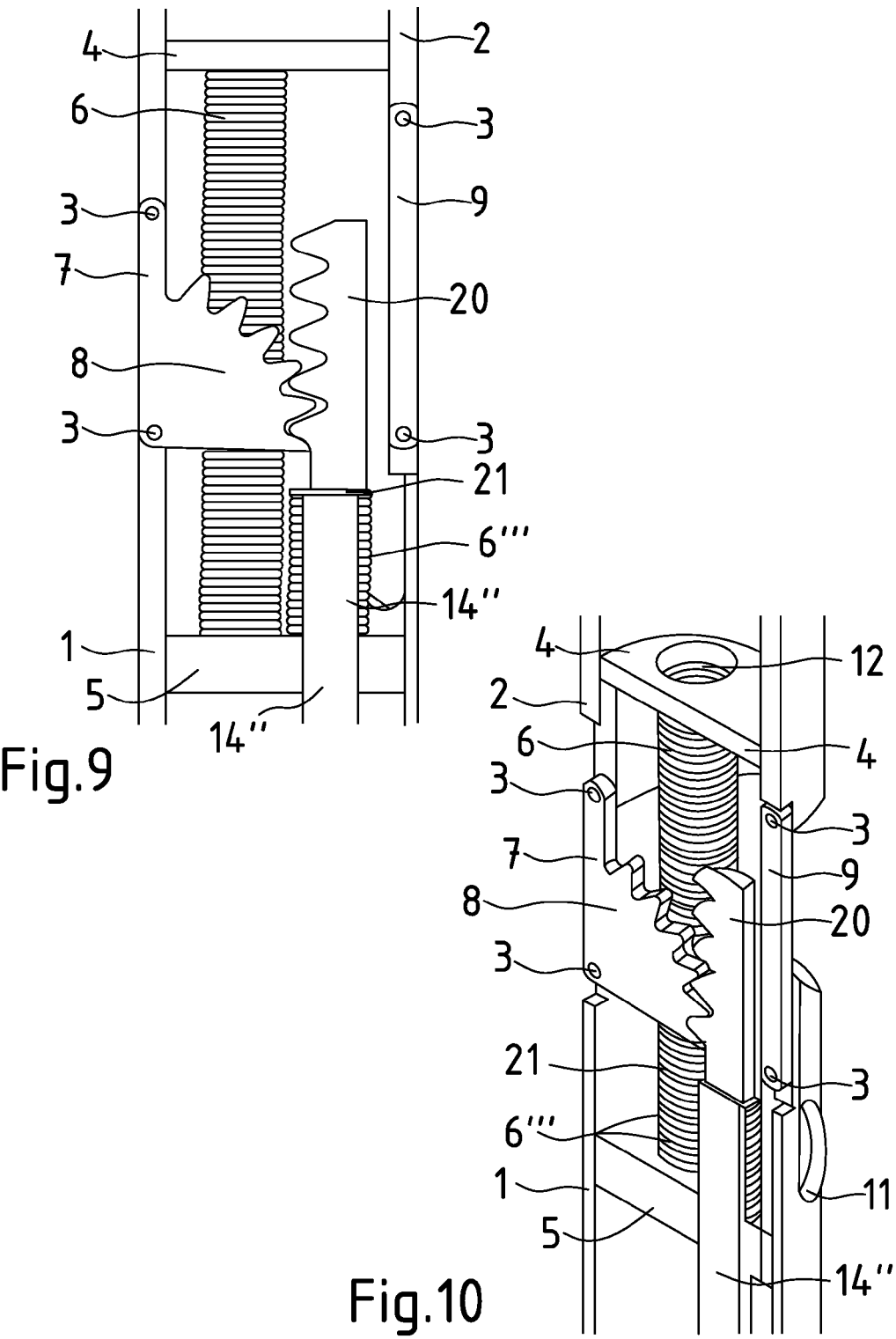

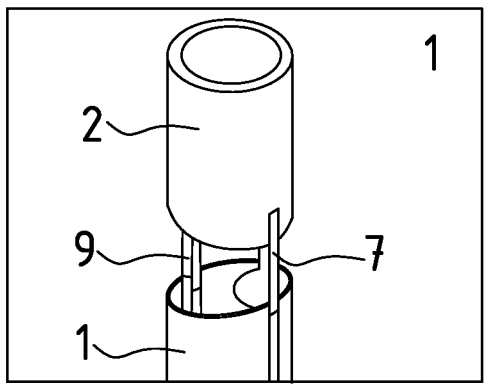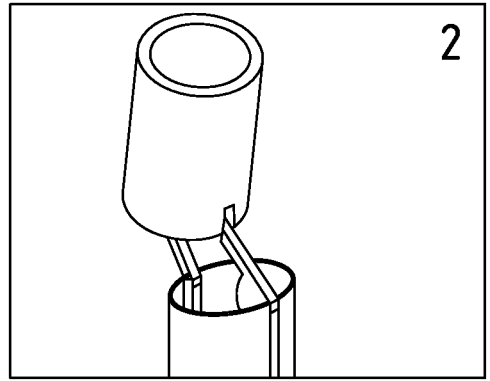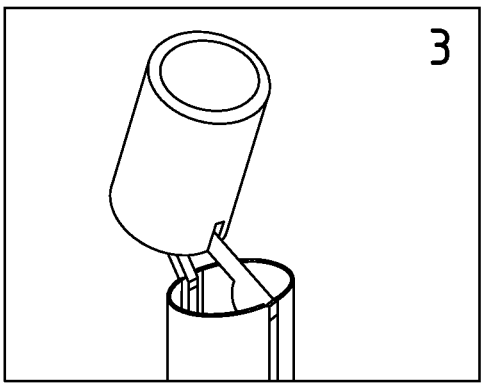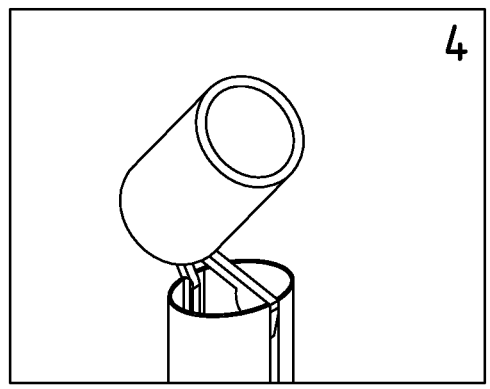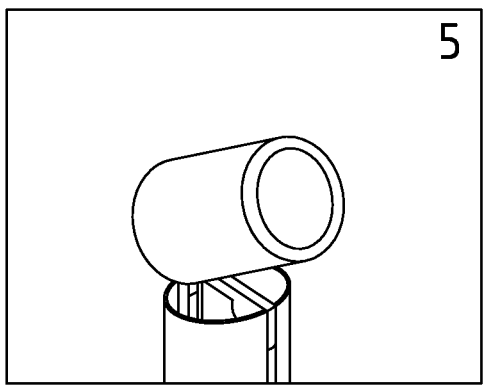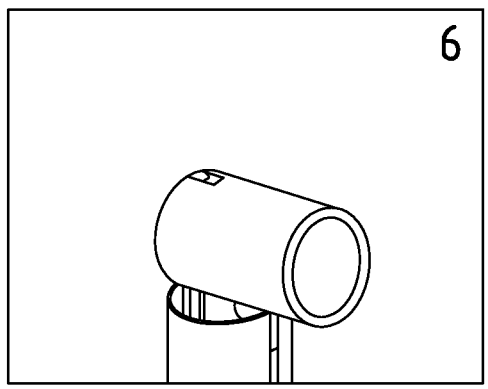
Fig.13

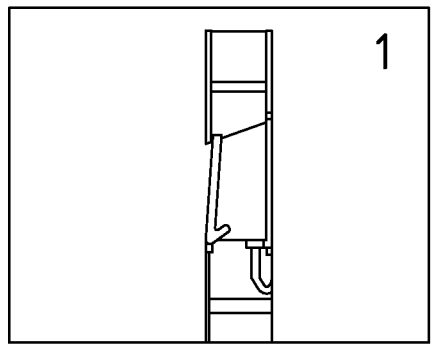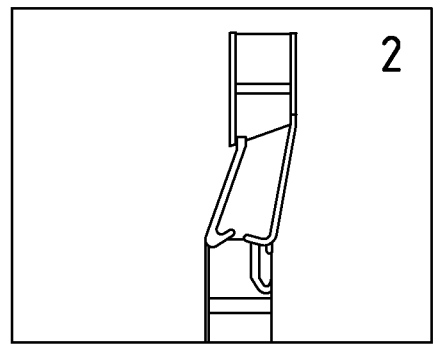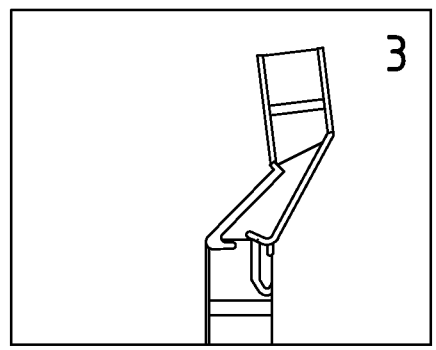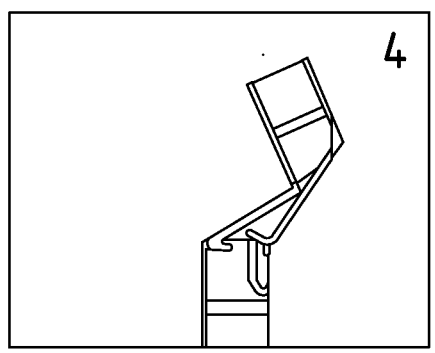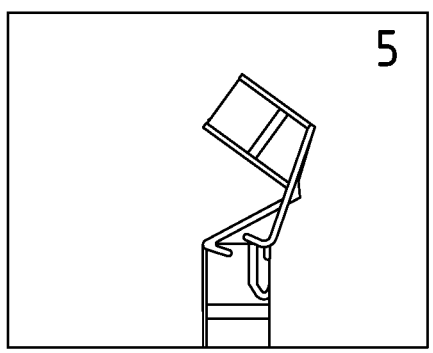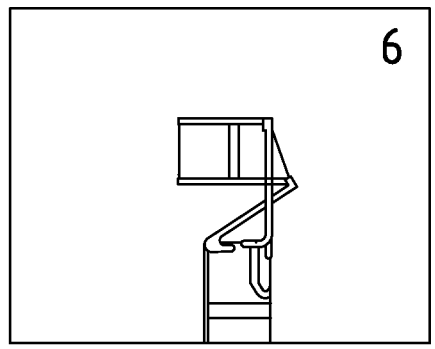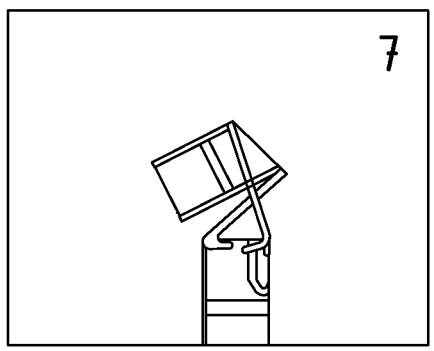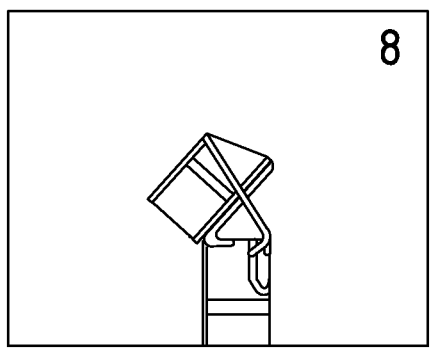
Fig.14

JOINTED PORTION OF A SHAFT FOR AN ENDOSCOPIC INSTRUMENT

CROSS-REFERENCE TO RELATED APPLICATIONS

The present application claims priority of German patent application No. 10 2010 034 380.3 filed on Aug. 13, 2010, the content of which is incorporated herein by reference.

FIELD OF THE INVENTION

The present invention relates to a jointed portion of a shaft for an endoscopic instrument, in particular for an endoscope, according to the generic terms of claim 1, as well as an endoscopic instrument, in particular an endoscope, with such a jointed portion.

BACKGROUND OF THE INVENTION

Endoscopes are used today for a number of applications in medicine and technology. Endoscopes typically include a rigid or flexible elongated shaft, suitable for insertion into a cavity, having on its tip an endoscope lens to generate an image of a scene in the cavity being observed. To convey the endoscopic image onward from the distal end (that is, away from the observer) of the endoscope to the proximal end (close to the observer), that is, to the operating part, an arranged bundle of light-conducting fibers, for example, or, for rigid endoscopes, a system of rod lenses can be provided inside the shaft; on the proximal end of the endoscope the endoscopic image can be observed directly via an eyepiece or can be recorded by an electronic image recorder for further processing and display. An electronic image recorder, for example a CCD chip, can also be positioned in the area of the distal end of the shaft, that is, at the endoscope tip ("chip on the tip"); in this case, electrical supply and data lines of the image recorder run inside the shaft. Because, as a rule, insufficient light is available in the cavity being observed, a light-conducting system is also provided inside the shaft in order to transport sufficient light to the distal end of the endoscope, where it is used to illuminate the cavity. In addition, channels for endoscopic working instruments as well as, for example, lines for flushing and suction can be fed through the shaft all the way to the distal end of the endoscope shaft. In addition, an endoscope typically includes an operating part that is positioned on the proximal end of the shaft and is usually configured as a handle. Said operating part can, for example, comprise operating elements for controlling the image recorder, an endoscopic video camera and/or junctions for power and data lines, for an external light source and/or for flushing and suction pumps.

Depending on the purpose of the use and the accessibility of the cavity that is to be observed, rigid or flexible endoscopes are used. Here the viewing angle for rigid endoscopes is as a rule determined by the configuration of the object lens. In a number of applications, however, it is desirable to be able to bend the distal end of the endoscope shaft, that is, the endoscope tip, to be able to change not just the alignment of the endoscope tip but also the viewing angle of a lens positioned in the endoscope tip. In flexible endoscopes it is known how to configure a partial area of the shaft, in particular the distal end area of the shaft, so that it is actively bendable and thus can angle the endoscope tip. An area of the cavity can thereby be observed that is far greater than the angle of opening of the observation lens. As a result, better access can be gained to particular areas in the human body that cannot be observed, or can only partly be observed, with a rigid endoscope, areas such as complex-shaped hollow organs like the stomach or digestive tract, as well as the insufflated abdomen during a laparoscopy.

The distal end area of the shaft of a flexible endoscope with bendable tip consists primarily of jointed connected ring elements, which form the supporting structure of the shaft and are operated and tipped toward one another by Bowden cables, also known as curve control wires. To facilitate insertion into the cavity and to prevent penetration by substances, the ring elements are surrounded by a flexible sheath made of a synthetic material. Inside the ring elements, light and image conducting cables are primarily run, along with channels for fluids or endoscopic working instruments. The curve control wires are fed along the outside or inside of the ring elements. Flexible endoscopes of this type are disclosed, for example, in U.S. Pat. No. 6,270,453 B1, U.S. Pat. No. 6,482,149 B1 or DE 101 43 966 B4.

It is also known in the art to bendably configure the distal end area of the shaft with the help of specially shaped bending elements, which can likewise be diverted by Bowden cables, as is described in U.S. Pat. No. 6,749,560 B1 and in EP 1 927 312 A1. It is known from U.S. Pat. No. 5,885,207 A1, U.S. Pat. No. 6,550,193 B1 and U.S. Pat. No. 6,860,849 B2 that the shaft of a flexible endoscope comprises a multi-layered supporting sheath that is made up of various materials with different material characteristic values that combine to form a controllable flexible shaft sheath. Self-resetting springs can also be used in configuring a controllable flexible shaft end, such that the control is likewise exerted by pull wires; endoscopes of this kind are disclosed, for example, in WO 2008/060075 A1 and EP 1 849 400 A1.

Here the minimum radius allowed for the curvable or divertible portion of the shaft is pre-determined by the particular construction principle. For example, a jointed portion made up of ring elements that are arranged one after the other and jointedly connected with one another allows only a relatively large bending radius because the individual ring elements each comprise only a small tipping angle to the next ring element. If the jointed connection of two elements allows only a tipping around one axis, then for a spatial bending capacity it is necessary to arrange elements with tipping axes pivoted alternatingly toward one another so that only each second element can be diverted in a particular desired direction; as a result, the possible minimum bending radius is again enlarged. The area close to the shaft end is therefore not visible with a lens positioned in the endoscope tip.

In the context of the present application, an endoscopic instrument is understood to be one that is suitable for insertion into a cavity and for observation inside the cavity and/or for performing manipulations inside the cavity, although the possibility of optical observation is not necessarily required to be present. Endoscopes for insertion into a cavity and for observation inside the cavity are among the endoscopic instruments in the meaning of the present invention.

SUMMARY OF THE INVENTION

It is the object of the present invention to provide a jointed portion of a shaft for an endoscopic instrument along with an endoscopic instrument, in particular an endoscope, to make it possible to observe even the close vicinity and/or to manipulate also in the area close to the shaft or of the shaft end.

This object is achieved by means of a jointed portion as well as by an endoscopic instrument, in particular an endoscope, in accordance with the claims.

A jointed portion of a shaft connects a proximal shaft part with a distal shaft part, for example a tip of the endoscopic instrument, in particular the endoscope, in a way to be angulated. According to the invention, the distal shaft part is connected with the proximal shaft part by two rigid jointed bars of different lengths, such that the jointed bars each attach by means of a joint on the distal and proximal shaft part, in particular on the distal end of the proximal shaft part and on the proximal end of the distal shaft. The jointed bars can be fixed to the respective shaft parts with rivets or bolts and can be angulated in the radial direction toward the inside and outside.

The joints are configured in particular as one-axis joints whose axes are parallel to one another and each are positioned across the longitudinal axis of the particular shaft part, that is, the jointed bars can pivot with respect to the distal end of the proximal shaft part around axes that are aligned approximately perpendicular to a longitudinal axis of the proximal shaft part or of its distal end area, and can pivot with respect to the proximal end of the distal shaft part around axes that are aligned approximately perpendicular to a longitudinal axis of the distal shaft part or of its distal end area.

Both parts of the shaft, in particular their respective ends, can be of cylindrical configuration. In particular, the distal shaft part can assume an elongated position in which it constitutes a straight continuation of the distal end area of the proximal shaft part. For this purpose the distal end of the proximal part of the shaft and/or the proximal end of the distal shaft part can be cut off diagonally. Both shaft parts can contain additional function elements such as mechanical elements for controlling the angling as well as lines for conveying light, power, and data.

Because the distal shaft part is connected with the proximal shaft part by two rigid pivotable jointed bars of different lengths, the distal shaft part and thus in particular an angulated tip of the endoscopic instrument, in particular the endoscope, can be controlled in such a way as to allow even an observation of the area close to the endoscope or of the endoscope shaft or manipulation in this area. A four-point jointed arrangement of this type combines a lateral displacement with the angling motion, so that the distal shaft part or the tip in an angling can be mounted contrary to the viewing angle of a lens positioned in the distal shaft part or in the endoscope tip. As a result, even areas very close to the endoscope shaft can be observed. This applies also to an instrument for manipulation.

According to a preferred embodiment of the invention, the angling of the tip can be controlled by a push rod that with another joint attaches at a lever or arm connected with one of the jointed bars. The other joint can, in particular, be a one-axis joint. The push rod is in particular configured for transmitting pushing and pulling motions and therefore is also referred to as a pull rod. By means of a pulling motion or a pushing motion of the push rod, the arm is tipped in proximal or distal direction and the jointed bar connected with the arm is correspondingly pivoted. Because of the four-point kinematics of the angulated tip, the second jointed bar follows the motion of the first, but at a different tipping angle because of the different lengths of the two jointed bars. The push rod for example can be of flexible configuration in portions and is preferably fed through the shaft as far as an operating part of the endoscopic instrument, in particular of the endoscope. On the operating part it is possible to position actuation elements and/or drives for sliding the push rod inside the shaft and thus for controlling the angling of the distal shaft part or of the angulated tip.

In an especially preferred manner, the arm is connected with one of the jointed bars in such a way that the pivot point of the push rod forms a maximum jointed arm in a center or preferred angle area of the angling with the pivot point of the jointed bar on the proximal shaft part. In the process, the preferred angle area can be determined for example by a preferred viewing angle of a lens positioned in the angulated tip. For example, the jointed bar can be positioned to pivot by 90 degrees and the arm at an angle of 45 degrees on the end of the jointed bar connected with the proximal shaft part. Because of such an arrangement of the arm, an especially sensitive control of the motion of the distal shaft part or of an angulated tip becomes possible.

In addition, it is advantageous if the arm is applied on the shorter of the two jointed bars of different lengths, because said arm in angling executes the greater angled motion and thus a more sensitive control is possible. In particular, the arm is positioned on the proximal end of the shorter jointed bar in such a way that it points cross-wise inward in the distal direction when the jointed portion is in elongated position. As a result, a push rod fed inside the shaft can make contact on the arm in especially simple manner. Here the arm can be of flexible construction to compensate for the crosswise motion of the pivot point of the push rod.

According to an alternative embodiment of the invention, the angling of the distal shaft part can be controlled by a push rod with whose distal end a toothed bar is connected that engages in a toothed wheel connected with one of the jointed bars or in a part of a toothed wheel. The toothed wheel is preferably positioned on the proximal end of the shorter of the two jointed bars, such that the center point of the toothed wheel coincides with the pivot point of the short jointed bar. The toothed wheel is in particular configured as a sector of a toothed wheel. The toothed rod, which can be of round or rectangular configuration for example, engages in the toothed wheel and can rotate it by axial pushing so that the short jointed bar connected with the toothed wheel is pivoted. This embodiment has the advantage that in the angling no crosswise motion of the distal end of the push rod occurs. The push rod fed through the shaft can be of flexible configuration, at least in some portions.

According to an additional alternative embodiment of the invention, the angling of the angulated tip can be controlled by a rotatable shaft with whose distal end a threaded rod or threaded bar is connected that engages in a toothed wheel connected with one of the jointed bars. The jointed bar and the toothed wheel or the toothed wheel segment connected with said bar can be of similar configuration as in the aforementioned embodiment. The jointed bar is thus pivoted by the toothed wheel by rotating the rotatable shaft as in a worm drive. In the process, the engaging of the threaded bar in the toothed wheel can remain restricted to a short area, in particular the distal area of the threaded bar. The rotatable shaft can also be of flexible configuration. This embodiment has the advantage that an especially sensitive control of the angling is possible through corresponding selection of the thread pitch.

In preferred manner the rotatable shaft is mounted so that it can be slid axially with respect to the proximal part of the shaft. This makes it possible, even with a failure or blocking of the rotation of the threaded bar, to push said bar axially somewhat like a toothed rod in order to bring the distal shaft part into an elongated position, which at least allows the shaft to be pulled out of the cavity.

According to an embodiment of the invention, the shorter of the two jointed bars corresponds to a distance shorter than the diameter of the shaft. In particular, the short jointed bar is shorter than the diameter of the proximal shaft part in its distal end area and likewise shorter than the diameter of the distal shaft part in its proximal end area. This has the advantage that the angling of the tip of the endoscopic instrument can occur without any danger of a blockage in a particular angle position.

According to another embodiment of the invention, both jointed bars are longer than a diameter of the shaft, in particular than the diameter of the distal end area of the proximal shaft part and the diameter of the proximal end area of the distal shaft part. Consequently, an angling of the tip is also possible well beyond 90 degrees. For this purpose, preferably both bars can be actuated by a displacement mechanism, which for example includes an arm extending laterally from the jointed bar or a toothed wheel on which a push rod engages by means of an additional joint or a toothed rod or a threaded bar. Both jointed bars here are powered alternately. At small anglings the short jointed bar is powered, but from a particular angle position the long bar assumes the control of the angling before the short bar can become blocked because of the kinematic connections.

To prevent the short, inwardly tipping bar from settling on the long bar, at least one of the bars can be divided in the longitudinal direction of the bar, for example in similar shape to a tuning fork. As a result, the two bars are intertwined into one another so that a more pronounced angling of the tip of the endoscopic instrument is possible.

According to an additional preferred embodiment of the invention, the two jointed bars attach in border areas of the respective shaft part that are opposite to one another. In particular, the distal end area of the proximal shaft part and the proximal end area of the distal shaft part can each comprises an approximately cylindrical outer shaft on which the jointed bars are each jointed nearly opposite one another. As a result, a particularly favorable gear ratio and thus a high stability of the arrangement from the ends of the two shaft parts and the two joint bars are achieved; on the other hand, the inner space of the particular shaft parts is available without substantial restrictions for the mechanism to control the angling and possibly for further elements.

Advantageously, between the proximal and the distal shaft parts, flexible lines are run that make possible a connection of optical and electronic components positioned in the distal shaft part, in particular in the tip of the endoscopic instrument, in particular the endoscope tip, with the proximal shaft part and then with the operating part of the endoscopic instrument, in particular the endoscope, or with devices that can be connected thereto. In particular, in the angulated tip, a video unit is positioned with optic elements such as lenses as well as, for example, a CCD chip as image recorder. The digital image signal in this case is fed by a data-conducting cable to the proximal end of the endoscope for further evaluation or observation by the user. Or else an endoscope object lens with an image conductor could be positioned in the endoscope tip by flexible fiberglass strands that are secured against local displacement. To illuminate the cavity that is to be observed, as a rule an illuminating lens is provided along with illuminating light conductors that are fed to the endoscope tip. In addition, additional supply and/or data lines as well as channels, for example, for rinsing or exhaust or for flexible endoscopic working instruments can be fed between the proximal and distal shaft parts as flexible lines.

It is further preferable that recesses should be made in the border area of the distal end of the proximal shaft part, in particular on the distal end of an outer shaft of the proximal shaft part, and in said recesses the flexible lines should be placed upon angling of the distal shaft part. In an angling, the distal shaft part can be displaced in a configuration based on the example of an endoscope in such a way that its distal end, which preferably comprises the window of the endoscope object lens and the outlet openings of the illuminating light conductor or of the instrument and other channels, comes to lie approximately as an extension of an outer contour of the distal end of the proximal shaft part. In the straightened position the proximal area of the distal shaft part or of the endoscope tip in this case is displaced in contrary sense and can extend beyond the extended outer contour of the distal end of the proximal part of the endoscopic shaft. Also the flexible lines, which run between the shaft and the angulated tip, can therefore extend out beyond the outer contour. In order to feed these lines, which comprise a certain bending radius, in the proximal shaft part, therefore one or more recesses are provided on the rand area of the distal end of the proximal shaft part, such that into such recesses the lines can be inserted in an angling of the distal shaft part. The bending radius of the lines is thereby displaced during an angling to some extent onto the side opposite to the viewing angle and the area to be observed. Therefore the bending radius does not restrict the angling of the endoscope tip, and therefore an angling is possible around a large angle and areas in the immediate vicinity of the endoscope shaft can be observed.

In preferred manner, the flexible lines are enclosed by one or more insulated flexible sleeves, which offer protection of the lines from mechanical damage as well as from penetration of impurities or liquids in use of the endoscopic instrument, in particular of the endoscope, as well as from penetration of cleaning and disinfecting fluids or steam in cleaning and sterilization. In particular, each of the lines can be enclosed by a separate flexible sleeve, or more or even all lines can be enclosed by a flexible sleeve. The flexible sleeve can, for example, be configured as a preferably metallic bellows. Also the jointed bars and/or the arm or other elements of the displacement mechanism can be insulated by one or more flexible sleeves, for example bellows. By appropriate manufacture of the flexible sleeves can make it possible for the endoscopic instruments or the envelope to be autoclavable.

According to an especially preferred embodiment of the invention, the distal and proximal parts of the shaft are each separately insulated from outside, in particular insulated from liquids and steam. As a result there are two separate areas, insulated from the outside. The lines that are fed through the distal and proximal shaft parts as well as in some cases the actuation mechanism for the angling of the jointed bars themselves can be protected by flexible sleeves, which in turn are insulated and connected with the two insulated areas. As a result a comprehensive protection from penetration of substances and from mechanical damage can be achieved as well as a further improvement in resistance to autoclaving.

In advantageous manner, on the proximal side of the distal shaft part and/or on the distal end of the proximal shaft part an insulating plane is provided, which is displaced from the respective end portion inward, that is, from the proximal end of the distal shaft part in the distal direction or from the distal end of the proximal shaft part in the proximal direction.

Consequently, also in an angling of the distal shaft part around a great angle, a sufficiently large bending radius of the flexible lines becomes constantly possible and in addition a sufficient moving space for the jointed bars is provided. The insulating planes can lie crosswise in the respect shaft part or in the tip of the endoscopic instrument or can be positioned perpendicular to the respective longitudinal axis. They are connected by a steam-insulated connection, for example by soldering, with an inside of a respective outer shaft.

An inventive endoscopic instrument, in particular an endoscope, comprises a shaft, in particular an endoscope shaft, configured for insertion into a cavity, and an operating part. The shaft comprises an inventive jointed portion for angling of a distal shaft part, for example a controllable endoscope tip, with respect to a proximal shaft part. The operating part can comprise operating elements, for example for actuating the angling of the distal shaft part by a sliding of the push rod or a rotation of the rotatable shaft. In addition the operating part can comprise junctions, for example for a video camera unit, for suction and rinsing pumps and/or for endoscopic working instruments. The operating part is in particular configured as a handle.

It is understood that the aforementioned characteristics and those yet to be presented can be applied not just in the particular indicated combination but also in other combinations or independently, without departing from the framework of the present invention.

Additional aspects of the invention can be seen from the following description of a preferred embodiment and the appended drawings, which are as follows.

BRIEF DESCRIPTION OF THE DRAWINGS

FIG. 9 shows a side sectional view of the jointed portion according to a fourth embodiment.

FIG. 10 shows an isometric view of the jointed portion of the fourth embodiment.

FIG. 13 shows a schematic isometric depiction of the motion sequence in an inventive jointed portion.

FIG. 14 shows schematic side sectional views to clarify the motion sequence in a jointed portion according to an additional embodiment of the invention.

DETAILED DESCRIPTION OF THE INVENTION

Figure 1:
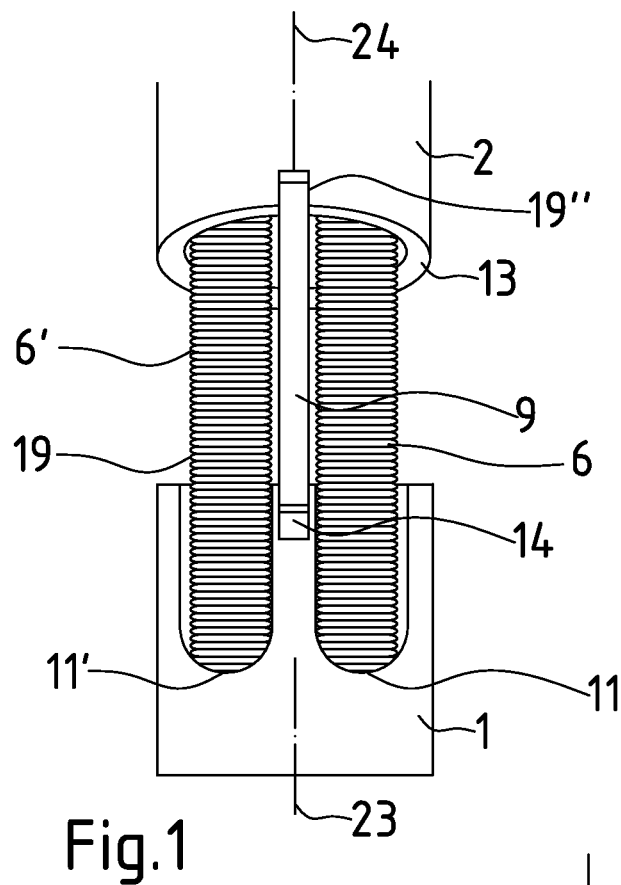
FIG. 1 shows a rear view of a jointed portion according to a first embodiment of the invention.
Figure 2:
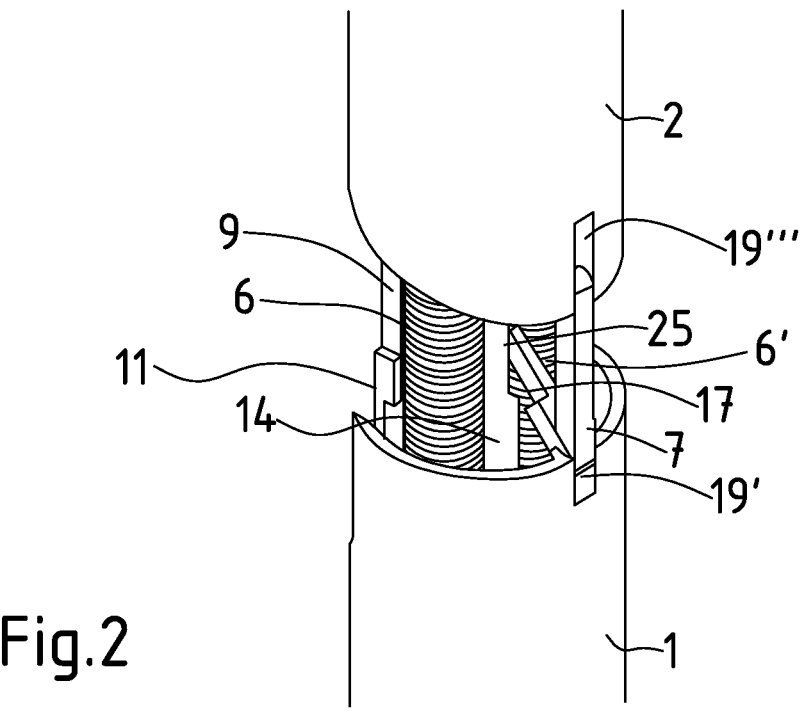
FIG. 2 shows an isometric view of the jointed portion according to the first embodiment.

As is shown in FIGS. 1 and 2, the jointed portion of a shaft of an endoscopic instrument, in particular of an endoscope, according to a first embodiment of the invention comprises two jointed bars 7, 9, which produce a jointed connection between a proximal part 1 and a distal part 2 of the shaft. In FIGS. 1 through 12, the distal end area of the proximal shaft part 1 and the proximal end area of the distal shaft part 2 are each shown. The proximal shaft part 1 can be connected by its proximal end with an operating part (not illustrated). The distal shaft part 2 can be the tip of the endoscopic instrument or can be connected with it. Located in the tip of the endoscopic instrument, in particular of the endoscope, is a video unit as well as the outlets of the other channels (not illustrated).

As shown in FIG. 1, in the outer shaft of the proximal shaft part 1 two grooves 19, 19' are provided that allow the jointed bars 7, 9 to fit in and are sufficiently finished so that they will not prevent the joint from folding together during the angling. The jointed bars can be pivoted in the grooves 19, 19', each around an axis perpendicular to the longitudinal axis 23 of the distal end of the proximal shaft part 1. Corresponding thereto, a groove 19'' is provided in a cylindrical outer tube of the distal shaft part 2 for inserting the distal end of the jointed bar 9, and in said groove the jointed bar is mounted so that it can pivot around an axis that is perpendicular to the longitudinal axis 24 of the proximal end of the distal shaft part 2 and parallel to the pivot axis in the proximal shaft part. A corresponding groove for accepting the other jointed bar 7 and securing a pivot axis, which is likewise parallel thereto, is covered up in the view in FIG. 1.

According to FIGS. 1 and 2, lines for power, data and light run between the two shaft parts 1, 2, along with other channels that are protected by two bellows or spring bellows 6, 6'. The bellows 6, 6' are positioned opposite one another in relation to the plane of the jointed bars, so that the deflecting arm 17 and the push rod 14 run between the bellows. As can be recognized in particular in FIG. 1, the cylindrical outer shaft of the proximal shaft part 1 comprises two recesses 11, 11' on its rear side, that is, in the angled position, the side opposite a viewing direction of the lens positioned in the endoscope tip, and the two bellows 6, 6' can be fitted into said recesses when the distal shaft part 2 is deflected, in order to avoid being creased or compressed during the angling process. Only the dorsal jointed bar 9 can be recognized in FIG. 1. The distal shaft part 2 comprises a crosswise closing surface 13 on its proximal end.

An isometric total view of the jointed area is illustrated in FIG. 2. The frontal jointed bar 7 comprises a lever or deflecting arm 17 on which a push rod 14 that can be powered is affixed, in order to deflect the frontal jointed bar 7 and thus the entire joint by means of the arm 17. Also recognizable in FIG. 2 are the frontal and dorsal grooves 19, 19' of the shaft of the endoscopic instrument that is configured as an endoscope shaft 1 and the frontal groove 19''' of the tip of the endoscopic instrument that is configured as an endoscope tip 2. The push rod 14 engages by means of a rotary joint 25 on the deflecting arm 17 of the shorter frontal jointed bar 7. To prevent a restriction of the pivot angle range, the push rod 14 and deflecting arm 17, as shown in FIG. 2, each comprise flattened areas or recesses in the area of the rotary joint 25.

In the elongated, that is, not angled, position shown in FIGS. 1 and 2, the distal shaft part 2 lies in a straight extension of the proximal shaft part 1, so that the respective longitudinal axes 23, 24 coincide and the respective outer contours lie on a common cylindrical surface. By pulling on the push rod 14 from the position shown in FIGS. 1 and 2 in the proximal direction, the distal shaft part can be angled in the frontal direction. The elongated position in each case is also shown in FIGS. 3 through 12.

Figure 3:
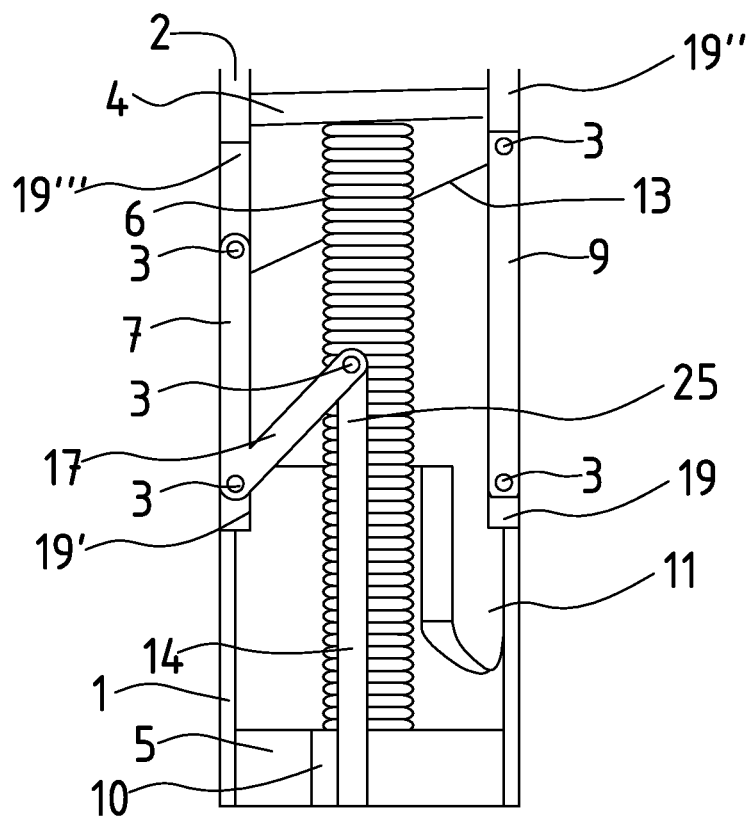
FIG. 3 shows a side sectional view through the jointed portion according to the first embodiment.
Figure 4:
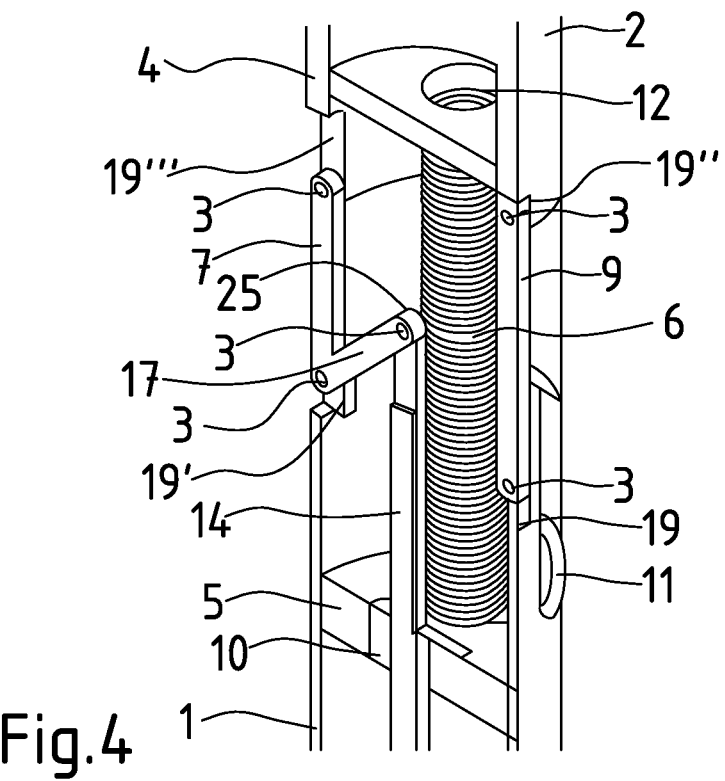
FIG. 4 shows an isometric sectional view in the folding plane of the jointed portion according to the first embodiment.

In FIG. 3, to clarify the jointed structure and powering with the push rod, a side sectional view of the joint is shown according to the first embodiment, such that, according to FIGS. 3 and 4, actions for insulating can be taken. The distal part 1 and the proximal part 2 of the shaft are accordingly each sealed on their proximal or distal end by insulating planes 4, 5 to prevent penetration of substances. The two areas are connected to one another by the spring bellows 6. For this purpose the spring bellows 6 is inserted for insulating into the insulating planes 4, 5. The frontal, short jointed bar 7 and the dorsal, long jointed bar 9 are each rotatably mounted with rivets 3 on the proximal shaft part 1 and on the distal shaft part 2. The push rod 14 and the deflecting arm 17, which is at a 45 degree angle to the frontal jointed bar 7, are also rotatably connected with one another by a rivet 3. The push rod 14 is of flexible construction in order to be able to join in a slight cross-motion of the rotary joint 25 during the axial sliding. An insulation 10 in the proximal insulating plane 5, which allows the push rod 14 to be slid, prevents penetration of substances into the proximal shaft part 1. The insulating planes 4, 5 are displaced from the respective end area of the particular shaft part inward, that is, in the proximal direction in the proximal shaft part 1 and in distal direction in the distal shaft part 2, in order to allow sufficient space for movement for the arm 17, the push rod 14 and the bellows 6, 6'. The tapering 13 of the proximal end of the distal shaft part 2 is also clearly recognizable in FIG. 3.

In the isometric sectional view in FIG. 4, which makes clear the spatial proportions in the jointed portion, one can also recognize the opening 12 in the distal insulating plane 4, through which lines can run. The bellows 6, insulated from liquid and steam, is inserted into the opening 12. Provided in the proximal insulating plane 5 is a corresponding opening into which the bellows, likewise insulated from liquid and steam, is inserted.

Figure 5:
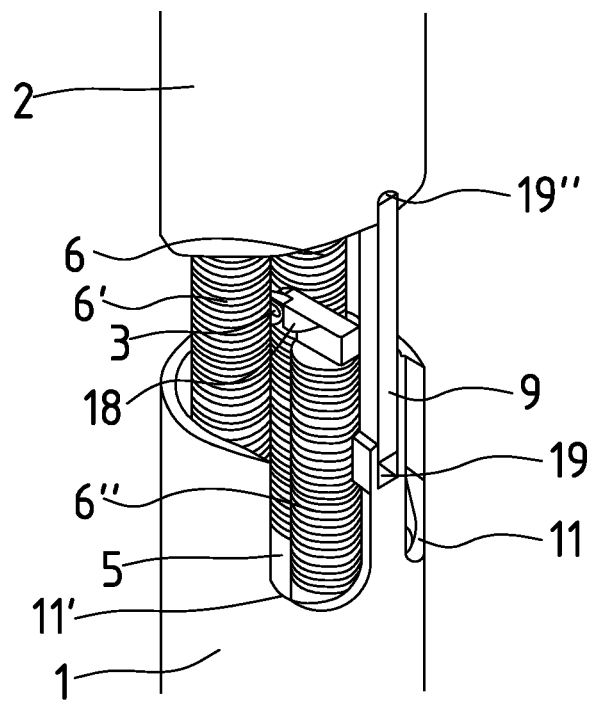
FIG. 5 shows an isometric overall view of the jointed portion according to a second embodiment of the invention.
Figure 6:
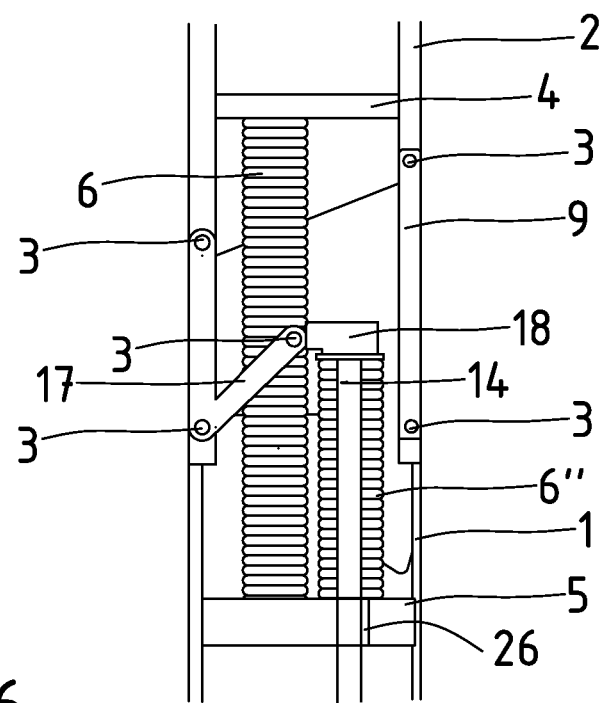
FIG. 6 shows a side sectional view along the folding plane of the jointed portion according to the second embodiment.

To prevent penetration by steam during autoclaving into the shaft and in particular into the endoscope shaft 1, in the variant illustrated in FIGS. 5 and 6 an additional bellows 6" is inserted by means of the push rod 14. Because the bellows 6, 6', 6", insulated against steam, are applied on the insulating planes 4, 5, these transitions remain secure from steam penetration. The bellows 6" of the push rod 14 is closed off with an applied piece 18 on whose underside the push rod 14 is fastened and whose upper part is jointedly connected laterally with the deflecting arm 17 of the frontal jointed bar 7 by a rivet 3. Insulation as in FIGS. 3 and 4 inside the proximal insulating plane 5 is not necessary in this case because of the insulation of the bellows 6". Therefore, as shown in FIG. 6, for passage of the push rod 14 through the proximal insulating plane 6, a larger passageway 26 can be provided to allow lateral play for the push rod 14. In this way less flexibility of the push rod 14 is sufficient to compensate with the bellows 6" for the crossways motion during the deflection motion. For reasons of space, in this embodiment both bellows 6, 6' are slightly displaced in the frontal direction for the passage of the lines in order to ensure sufficient space for the third bellows 6", which is dorsally displaced, by the push rod 14. Here sufficient distance is available so that the bellows 6, 6', 6" do not touch or impede one another during the angling motion and the bellows 6, 6' can enter the recesses 11, 11'.

Figure 7:
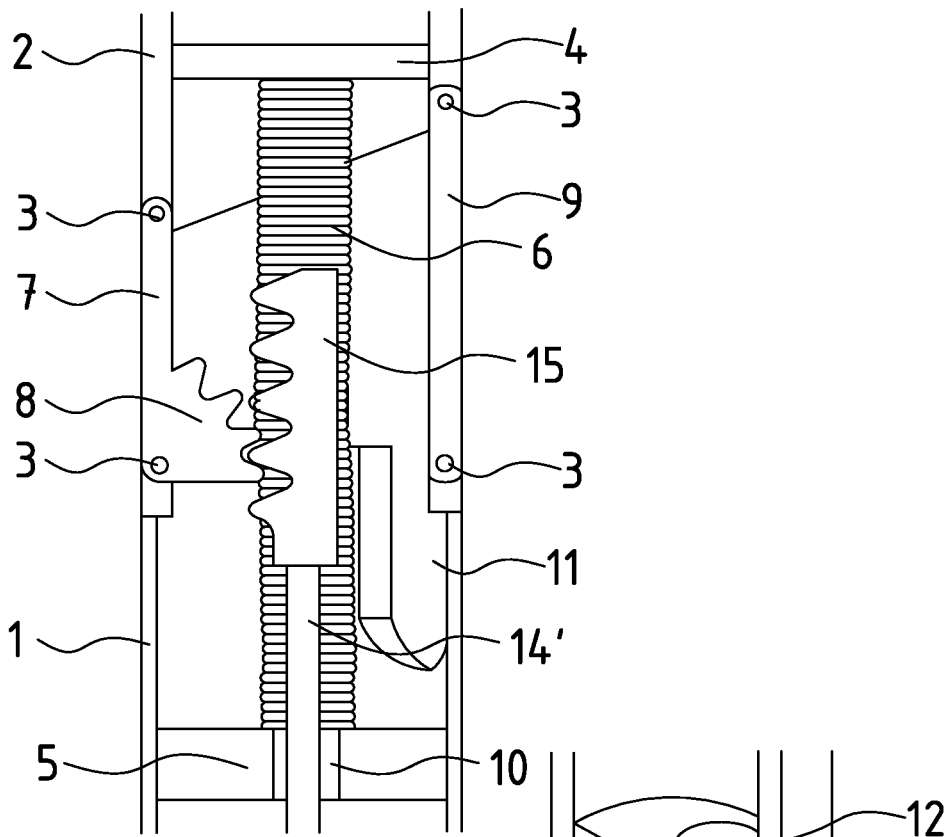
FIG. 7 shows a side sectional view of the jointed portion according to a third embodiment of the invention.
Figure 8:
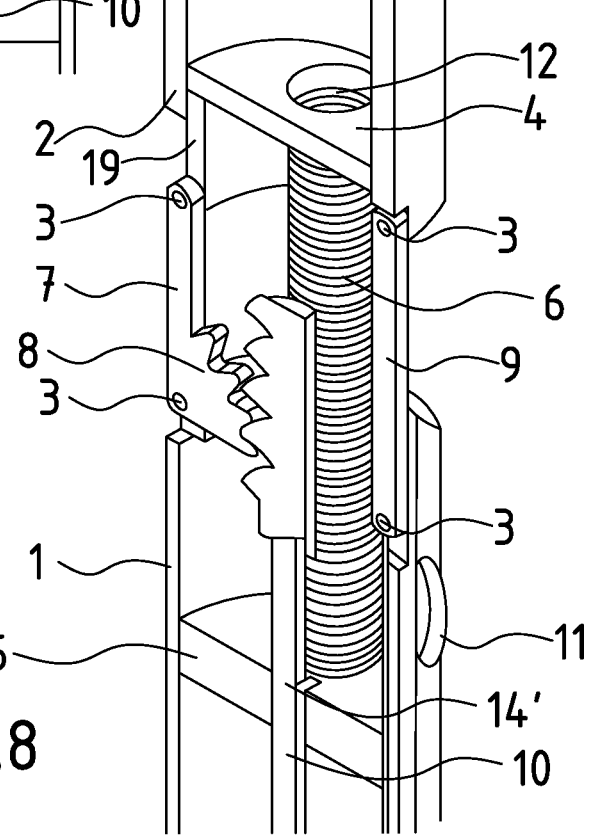
FIG. 8 shows an isometric view of the jointed portion of the third embodiment.

A third embodiment of the invention is shown in FIGS. 7 and 8. According to FIGS. 7 and 8, the frontal jointed bar 7, instead of a deflecting arm, comprises a toothed wheel segment 8 whose center point coincides with the rotation point of the bar 7. A toothed rod 15 engages in the toothed wheel segment 8 and is connected with the distal end of a push rod 14'; the push rod 14' can be configured as a single piece with the toothed rod 15. The push rod 14' runs through an insulation 10 in the proximal insulating plane 5. A crosswise motion does not occur in this embodiment, and therefore the push rod 14' is not required to have flexibility in this area.

To improve insulation from steam during autoclaving, according to the fourth embodiment of the invention, illustrated in FIGS. 9 and 10, an additional bellows 6''' can be applied by means of a push rod 14" on the proximal insulating plane 5. It is sealed off, insulated from steam, with a covering plate 21 on whose underside the push rod 14" rests and on whose upper side a short toothed rod 20 is fastened. In this variant as well, the push rod 14" does not need the same flexibility as the push rod of the first embodiment, because here no crossways deflection is expected. In addition, no additional insulation is required in the proximal insulating plane 5 because the bellows 6''' ensures sufficient insulation.

Figure 11:
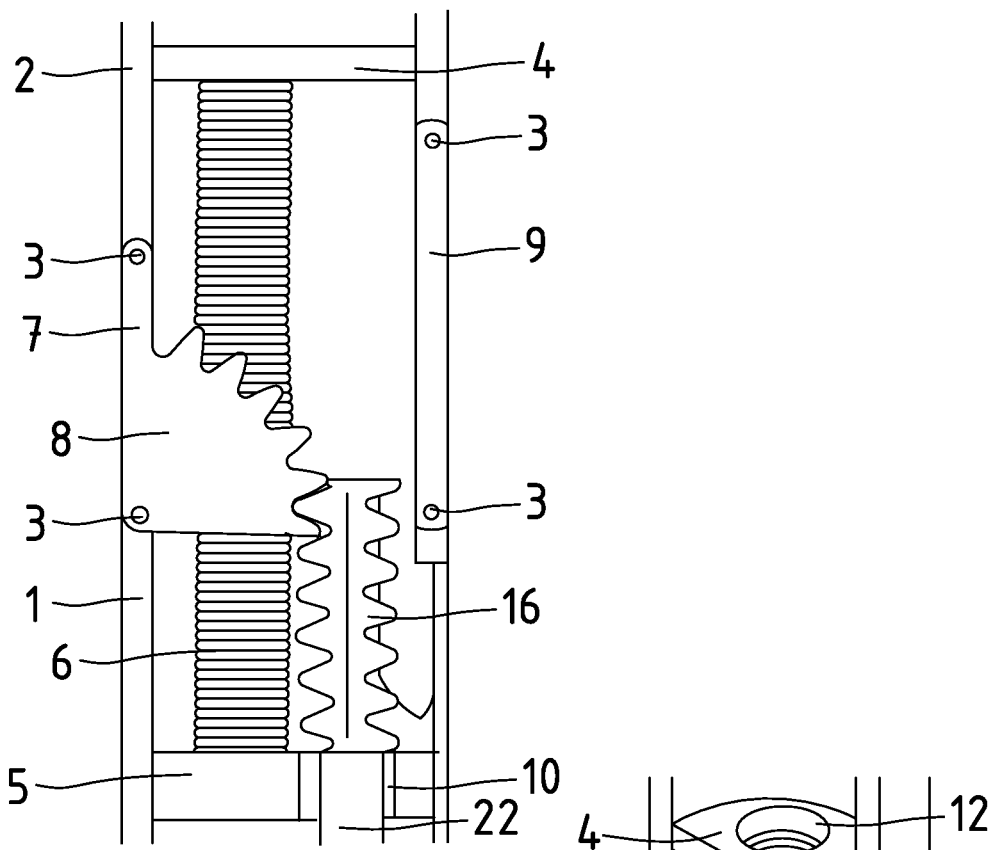
FIG. 11 shows a side sectional view of the jointed portion according to a fifth embodiment of the invention.
Figure 12:
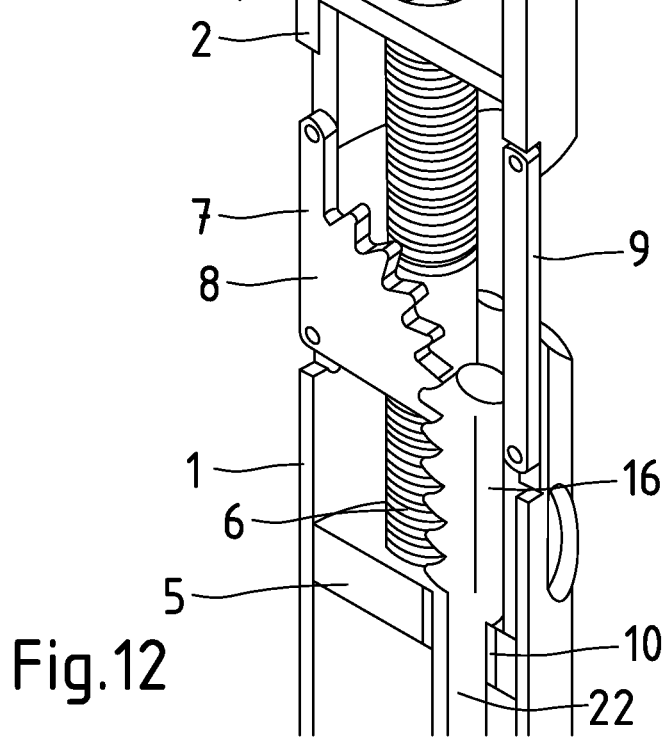
FIG. 12 shows an isometric view of the jointed portion of the fifth embodiment.

A fifth embodiment of the invention is illustrated in FIGS. 11 and 12. The actuated front jointed bar 7, here as well, comprises a toothed wheel segment 8, which for example can be larger than in the third and fourth embodiments, and by which a threaded rod 16 is moved as in a worm drive. According to a variant, the angling of the joint occurs by means of a rotation of the threaded rod 16, which is applied on a rotatable shaft 22 fed through the shaft. Said rotatable shaft runs through an insulation 10 in the proximal insulating plane 5 to prevent penetration of substances into the shaft, which is configured here as an endoscope shaft 1.

For reasons of space, both bellows 6, 6' and the threaded rod 16 are not positioned in a line but rather set off from one another, allowing sufficient distance so that the bellows 6, 6' upon deflection pass by the threaded rod 16 into the recesses 11, 11'. The threaded area of the threaded rod 16 needs to include only a few pitches because at all times only a few teeth of the toothed wheel segment 8 engage.

In the event that rotation of the threaded rod 16 should fail, provisions can be made so that it can nevertheless be slid axially like the toothed rod 15 in order to bring the tip 2 back into elongated position. For this reason it is advantageous that the threaded rod 16 should include more pitches than would be required for operation by rotation of the threaded rod 16.

As is shown schematically in FIG. 13 for a tip of the endoscopic instrument that is configured for angling up to about 90 degrees as an endoscope tip, the short bar 7 moves to angle the distal shaft part 2, which here constitutes the endoscope tip, from the elongated position (FIG. 13, partial image 1) radially inward around its proximal jointed point. Because of the coupling of the individual elements, the endoscope tip here displaces itself in dorsal direction (partial image 2). With increasing tipping motion of the short bar 7 inward, the sliding of the tip converts into a rotation (partial images 3 through 5). In the end position the tip is at approximately a 90 degree angle and displaced backward, that is dorsally (in partial image 6 seen from dorsal direction). The polycentric joint has thus folded itself up during the motion.

The bellows, not shown in FIG. 13 for the sake of simplicity, adapt themselves to the motion and follow the endoscope tip. They bend out dorsally behind the endoscope. The unavoidable bending radius of the light- and image-conducting cables is therefore to some extent displaced backward. To keep the pleated bellows here from being compressed and creased by the two shaft parts, recesses are made at the distal end of the proximal shaft part, into which the bellows can move during the angling (see FIGS. 1 through 12). Between the two recesses, some material remains upright in order to be able to apply the rear, longer bar on the proximal shaft part. Because of their spring properties, the two bellows act both to reset and to stiffen themselves against crossways motion. The extent of their extension backward and the resetting force during angling depend, among other factors, on their length. If the insulating planes according to FIGS. 3 through 13 are somewhat displaced inwardly into the shaft, the bellows can better distribute the bending over greater length so that the backward overhangings and the required application of force are reduced.

It is also possible to angle the tip or the endoscope tip outward by well over 90 degrees if both jointed bars of the four-point polycentrics are longer than the shaft diameter (see FIG. 14). For this purpose the longer jointed bar comprises a similar arm or toothed wheel segment as the shorter jointed bar and is powered in similar manner as the shorter jointed bar by its push rod or a rotatable shaft (not shown in FIG. 14). Here only one of the two jointed bars is actuated at this point in time by the corresponding push rod or rotatable shaft. Here as well, starting from the elongated position (FIG. 14, partial image 1), the displacement of the tip or of the endoscope tip (partial image 2) converts into a tipping motion (partial images 3 through 5). In the array shown in FIG. 14 the motion is not restricted to an angling up to 90 degrees (partial image 6) but instead goes farther (partial image 7) and can lead to a position of the distal end surface of the tip or of the endoscope tip in the immediate vicinity of the distal end of the proximal shaft part (partial image 8). Here, from a particular angle position, the actuating mechanism of the long bar takes over the angling before the short bar can be blocked for kinematic reasons. To prevent the inward-tipping short bar from colliding with the long bar, one of the bars, i.e. the long bar in the illustrated example, is partly divided in similar manner to a tuning fork. As a result, both jointed bars can be cross over one another and further angle the tip or endoscope tip. In this embodiment as well, the actuating elements can be insulated by bellows.

Identical or similar parts are each provided with the same reference numbers in the drawings. For the sake of clarity, not all reference numbers are entered in all drawings.

What is claimed is:

1. A jointed portion of a shaft for an endoscope, said jointed portion comprising:
    a distal part of the shaft for the endoscope, said distal part having an optical element contained therein to generate an image;
    a proximal part of the shaft for the endoscope;
    two rigid jointed bars of different lengths, each rigid jointed bar connecting the distal part of the shaft with the proximal part of the shaft in a way to be angulated;
    each rigid jointed bar having ends that are pivotally attached by joints within grooves in the distal and proximal parts;
    an arm extending from one of the rigid jointed bars;
    a push rod connected to the arm via an additional joint; and
    the push rod and the arm each having a recess in an area of the additional joint, the recess of the push rod being disposed in the recess of the arm.

2. The jointed portion according to claim 1, wherein an angling of the distal part of the shaft with respect to the proximal part of the shaft is controlled by the push rod.

3. The jointed portion according to claim 2, wherein the arm is connected with the shorter of the two rigid jointed bars.

4. The jointed portion according to claim 1, wherein the shorter of the two rigid jointed bars is shorter than a diameter of the shaft.

5. The jointed portion according to claim 1, wherein both rigid jointed bars are longer than a diameter of the shaft.

6. The jointed portion according to claim 5, wherein at least one of the rigid jointed bars is divided.

7. The jointed portion according to claim 1, wherein the two rigid jointed bars attach in border areas of the proximal and/or distal shaft part that are opposite one another.

8. The jointed portion according to claim 1, wherein flexible lines run between the proximal and distal shaft parts.

9. The jointed portion according to claim 8, wherein in the border area of the distal end of the proximal shaft part, recesses are configured into which the flexible lines move during angling of the distal shaft part.

10. The jointed portion according to claim 9, wherein the flexible lines are enclosed by one or more insulated flexible sleeves.

11. The jointed portion according to claim 8, wherein the flexible lines are enclosed by one or more insulated flexible sleeves.

12. The jointed portion according to claim 11, wherein the proximal and distal shaft parts are each separately insulated.

13. The jointed portion according to claim 12, wherein on each of the proximal and distal shaft parts an insulating plane is provided that is displaced in the proximal or distal direction from a distal end area of the proximal shaft part or from a proximal end area of the distal shaft part.

14. The jointed portion according to claim 1, wherein a proximal end of the distal part of the shaft and a distal end of the proximal part of the shaft are each sealed by an insulating plane.

15. The jointed portion according to claim 1, wherein the two rigid jointed bars are configured to angle the distal part of the shaft relative to the proximal part of the shaft by at least up to 90 degrees.

16. An endoscope comprising:
    a jointed portion including:
        a distal part of a shaft, said distal part having an optical element contained therein to generate an image;
        a proximal part of the shaft;
        two rigid jointed bars of different lengths, each rigid jointed bar connecting the distal part of the shaft with the proximal part of the shaft in a way to be angulated;
        each rigid jointed bar having ends that are pivotally attached by joints within grooves in the distal and proximal parts;
        an arm extending from one of the rigid jointed bars;
        a push rod connected to the arm via an additional joint; and
        the push rod and the arm each having a recess in an area of the additional joint, the recess of the push rod being disposed in the recess of the arm; and
    an operating portion, the operating portion having operating elements and/or junctions.

17. A jointed portion of a shaft for an endoscope, said jointed portion comprising:

two rigid jointed bars of different lengths, each rigid jointed bar connecting a distal part of the shaft with a proximal part of the shaft in a way to be angulated;
each rigid jointed bar having ends that are pivotally attached by joints within grooves in the distal and proximal parts;
an arm extending from one of the rigid jointed bars;
a push rod connected to the arm via an additional joint; and
the push rod and the arm each having a recess in an area of the additional joint, the recess of the push rod being disposed in the recess of the arm.

* * * * *